United States Patent
Malisch

(10) Patent No.: US 7,651,488 B2
(45) Date of Patent: Jan. 26, 2010

(54) APPARATUS AND METHODS FOR DILATING VASOSPASM OF SMALL INTRACRANIAL ARTERIES

(75) Inventor: Timothy Wayne Malisch, Chicago, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 463 days.

(21) Appl. No.: 10/942,069

(22) Filed: Sep. 15, 2004

(65) Prior Publication Data

US 2005/0059938 A1 Mar. 17, 2005

Related U.S. Application Data

(60) Provisional application No. 60/503,259, filed on Sep. 16, 2003.

(51) Int. Cl.
A61M 25/00 (2006.01)

(52) U.S. Cl. ....................... 604/523; 604/265

(58) Field of Classification Search ......... 604/523–527, 604/264, 265
See application file for complete search history.

(56) References Cited

U.S. PATENT DOCUMENTS

| | | | |
|---|---|---|---|
| 4,842,590 A * | 6/1989 | Tanabe et al. | 604/524 |
| 4,921,478 A | 5/1990 | Solano et al. | |
| 5,295,995 A | 3/1994 | Kleiman | |
| 5,843,050 A * | 12/1998 | Jones et al. | 604/525 |
| 5,888,436 A * | 3/1999 | Keith et al. | 264/103 |
| 5,976,120 A * | 11/1999 | Chow et al. | 604/525 |
| 6,296,631 B2 * | 10/2001 | Chow | 604/525 |
| 6,669,721 B1 | 12/2003 | Bose et al. | |
| 2002/0133111 A1 * | 9/2002 | Shadduck | 604/19 |

* cited by examiner

*Primary Examiner*—Nicholas D Lucchesi
*Assistant Examiner*—Theodore J Stigell
(74) *Attorney, Agent, or Firm*—Robert C. Haldiman; Husch Blackwell Sanders LLP

(57) ABSTRACT

A device and method for treatment of intracranial vasospasm is provided. The device is a microcatheter having a steeply tapered end and is thicker walled, and in a preferred embodiment is braided to provide greater pushability. In order to achieve a thicker walled catheter, in one embodiment, the inner lumen diameter can be reduced, leaving the outer diameter the same while in another embodiment the catheter is larger in outer diameter. In one embodiment, the microcatheter is coated with performance enhancing lubricant, such as a hydrophilic coating. Further, the microcatheter can also be coated with drugs and serve as a drug delivery device, drugs being embedded into vessel intima. In the use of the method of treatment, the device is fed into the smaller arterial vessels in the brain simultaneously dilating arteries of various caliber along the path of the catheter to relieve vasospasm; pharmacological agents can then be delivered by the microcatheter to further effect treatment.

14 Claims, 8 Drawing Sheets

APPARATUS AND METHODS FOR DILATING VASOSPASM OF SMALL INTRACRANIAL ARTERIES

BACKGROUND OF THE INVENTION

The present invention concerns a device and method for relieving vasospasm affecting the intracranial arteries. More particularly the present invention concerns a device and method of performing non-balloon angioplasty within tiny arteries so as to relieve intracranial vasospasm.

The arterial make up of the head, and more specifically of the brain, includes important routes that are, of necessity, small and tortuous in character. As such, intracranial brain artery networks are comprised of vessels having small diameters and almost "hairpin"-like turns.

Patients with ruptured brain aneurysms, known as subarachnoid hemorrhage (or SAH) can develop intracranial vasospasm as a delayed complication. In vasospasm, the arteries supplying the brain are narrowed as a result of constriction and/or thickening of the blood vessel wall. Because the narrowed vessel lumen restricts blood flow, lack of blood supply to the brain distally can result in a stroke.

Current management of vasospasm utilizes a combination of mechanical dilatation (angioplasty) and pharmacological intervention of the spastic vessels. Mechanical angioplasty is commonly performed with a microcatheter with a small balloon attached at its end. Balloon angioplasty is widely accepted to be a safe, effective and durable treatment for vasospasm, but it is limited in that the balloon microcatheters are by design larger diameter and stiffer than simple microcatheters. As such, these microcatheters usually cannot be steered into vessels that are smaller or more tortuous. In addition, these balloons are chosen based on the diameter when maximally inflated and it is difficult to inflate a balloon to a diameter less than its designed maximum. For these reasons, angioplasty of affected arteries is usually reserved for larger, proximal vessels, while smaller, more tortuous, more distal vessels are not mechanically treated.

At present, most angioplasty of arteries affected by intracranial vasospasm is performed with specialized low-radial-pressure, compliant balloon microcatheters, such as the Sentry, manufactured by Target/Boston Scientific and the Equinox, manufactured by MicroTherapeutics, Inc. However, even these specialized balloon microcatheters have not overcome all of the noted shortcomings in that the tip profile and stiffness of these devices still prevents them from being steered into small, tortuous vessels. Moreover, the balloons tend to inflate in an all-or-nothing manner, making it less desirable to, for example, use a 3.5 mm diameter balloon to dilate a vessel with a 2.5 mm normal diameter due to the potential risk of over dilatation.

In rare occurrences, some individual practitioners have performed angioplasty of small, tortuous, distal arteries simply by passing a microcatheter (without a balloon) through the vessel. However, this technique is often not helpful because currently available microcatheters have generally blunt tips and in general have too small an outer diameter to accomplish much angioplasty.

Chemical or pharmacological intervention is also practiced. For example, the affected arteries can be infused with vasodilating drugs, to facilitate opening of the arteries. Infusion can be carried out by direct infusion through use of a catheter or by placement of such chemicals on, for example, an angioplasty balloon such that the chemical is placed onto the affected area of the arteries. However, there are inherent limitations in that the bathing of tissue with dilating chemicals, while effective, is generally effective for only the short period while the chemical is present or is present in an effective amount.

BRIEF SUMMARY OF THE INVENTION

In accordance with the present invention, a microcatheter comprising a steep taper with a large shaft is provided. The microcatheter is thicker walled, and in a preferred embodiment is braided to provide greater pushability. In order to achieve a thicker walled catheter, in one embodiment, the inner lumen diameter can be reduced, leaving the outer diameter the same. In one embodiment, the microcatheter is coated with performance enhancing lubricant, such as a hydrophilic coating. Further, the microcatheter is also coated with drugs and serves as a drug delivery device, drugs being embedded into vessel intima. Such drugs as heparin, anti-platelet drugs and vasoactive drugs are used. The present invention comprises a microcatheter with no balloon, but designed with a wall thickness, tapered outer diameter and tip profile that would allow angioplasty of smaller, more tortuous vessels by the outer surface of the microcatheter shaft.

These and other features and advantages of the present invention will be apparent from the following detailed description, in conjunction with the appended claims.

BRIEF DESCRIPTION OF THE SEVERAL VIEWS OF THE DRAWINGS

The benefits and advantages of the present invention will become more readily apparent to those of ordinary skill in the relevant art after reviewing the following detailed description and accompanying drawings and photographs, all of which are referred to as figures, wherein.

DETAILED DESCRIPTION OF THE INVENTION

Figure 1:
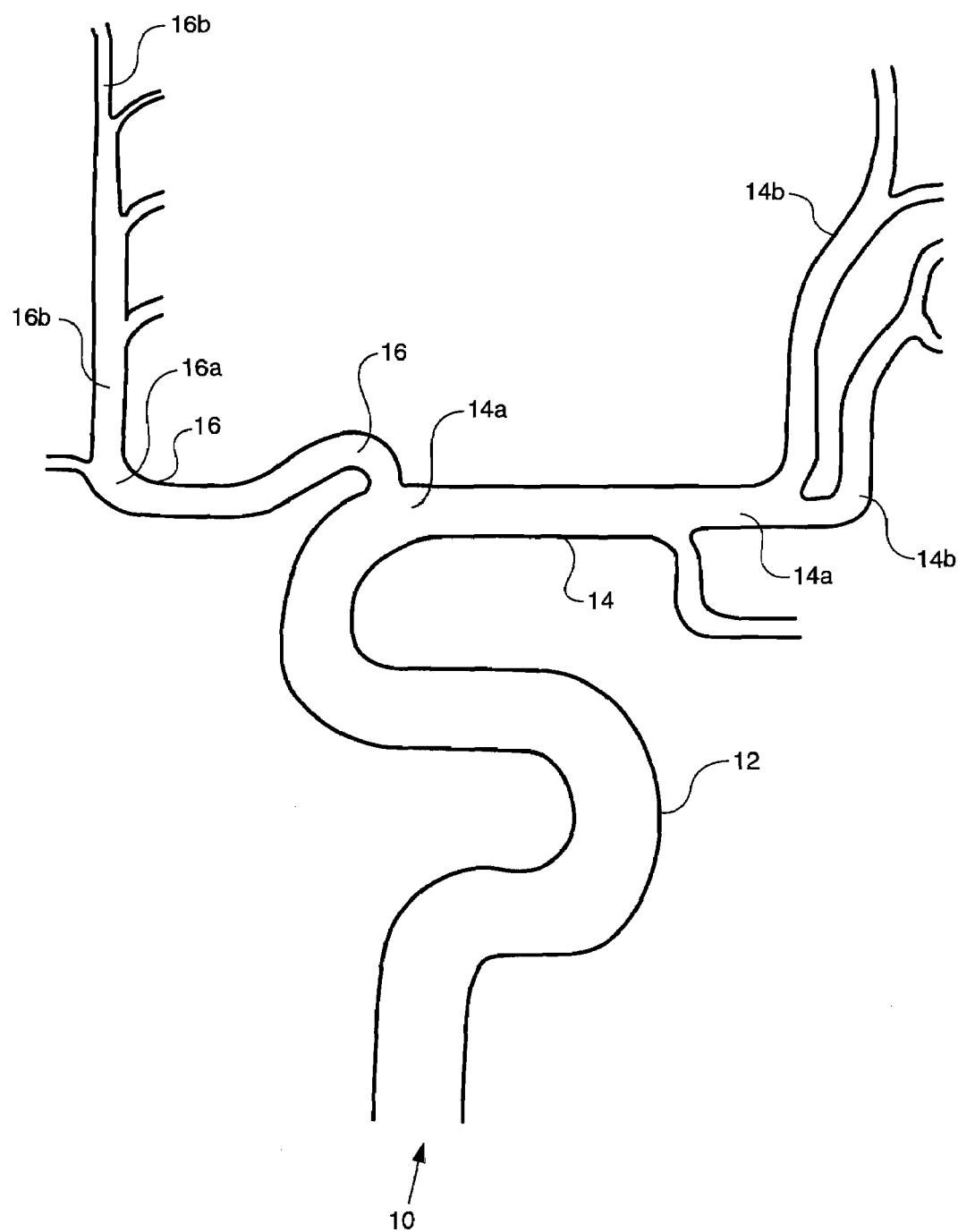
FIG. 1 is a schematic representation of the vascular anatomy of the brain showing typical branching pattern and vessel lumen diameters.

While the present invention is susceptible of embodiment in various forms, there is shown in the drawings and will hereinafter be described a presently preferred embodiment with the understanding that the present disclosure is to be considered an exemplification of the invention and is not intended to limit the invention to the specific embodiment illustrated.

It should be further understood that the title of this section of this specification, namely, "Detailed Description Of The Invention", relates to a requirement of the United States Patent Office, and does not imply, nor should be inferred to limit the subject matter disclosed herein.

Figure 2:
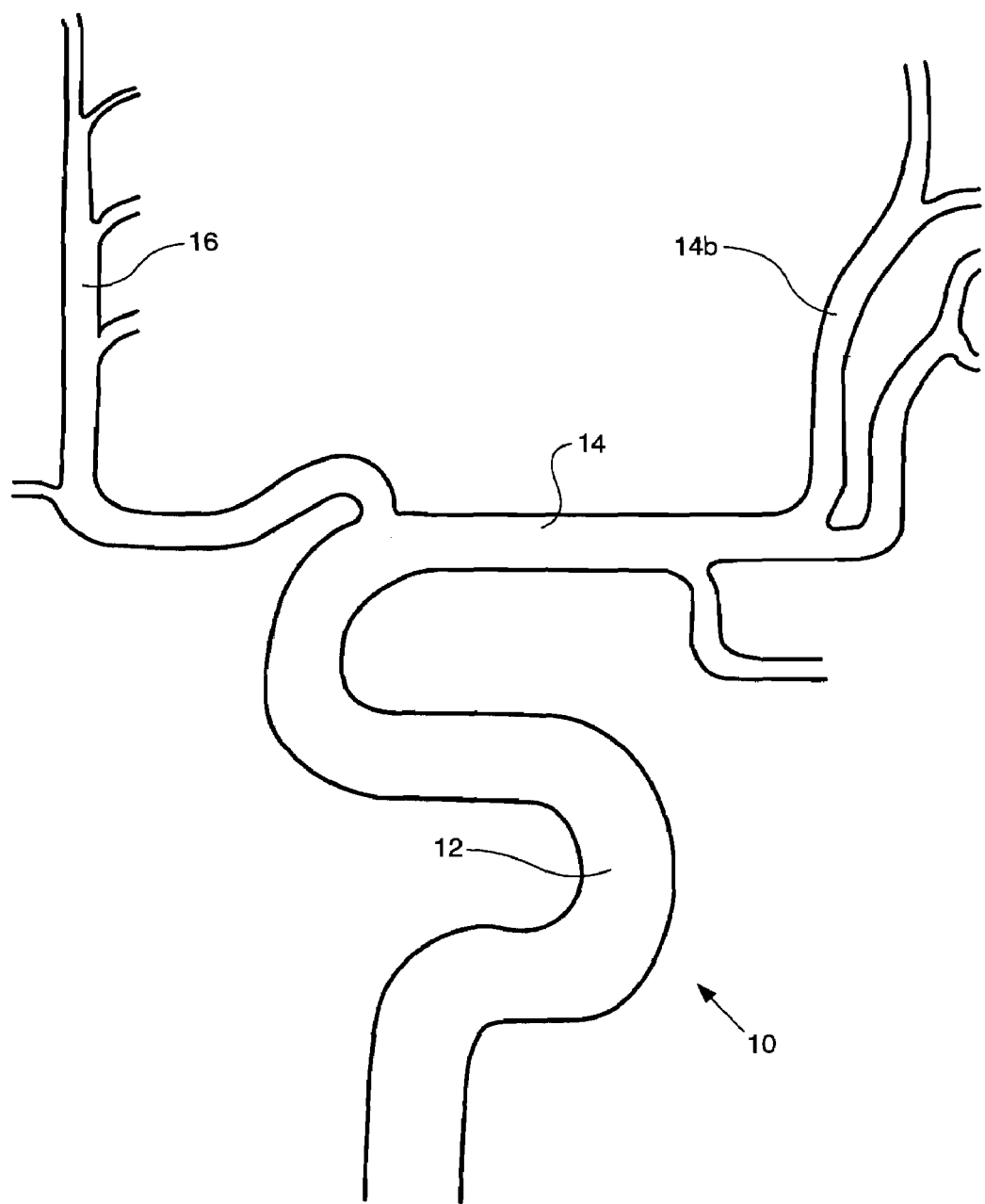
FIG. 2 is a schematic representation of the vascular anatomy of a healthy brain without vasospasm.

Referring to the figures, and in particular to FIGS. 1 and 2 there is shown the vascular anatomy 10 of a healthy brain, that is one not suffering from vasospasm, with a typical branching patterns and indications of vessel lumen diameters. It will be understood by persons having skill in the art that the FIG. 1 is a schematic representation of the brain and is not meant to be drawn to exact scale or be an exact representation of all healthy brain tissue.

As shown, the Internal Carotid Artery (ICA) 12 is a relatively large vessel having a vessel lumen diameter of about 4 mm to 5 mm. The two carotid arteries along with the two vertebral arteries are, in most patients, the four larger arteries at the base of the skull. The ICA 12 branches into the Middle Cerebral Artery (MCA) 14 and the Anterior Cerebral Artery (ACA) 16, each of which in turn branches into smaller arterial segments and passageways (first, second and third order branches).

The MCA 14 includes M1 segments 14a having vessel lumen diameters of about 2.5 mm to 3 mm and branches into a M2 segments 14b each of which has a reduced vessel lumen diameter of about 1.5 mm to 2.0 mm. ACA 16, as shown in FIG. 1, includes A1 segments 16a having vessel lumen diameters of about 1.5 mm to 2.0 mm and A2 segments 16b having reduced vessel lumen diameters of about 1.2 mm to 1.5 mm. As shown in FIGS. 1 and 2, other artery segments are also present having even smaller vessel lumen diameters.

Figure 3:
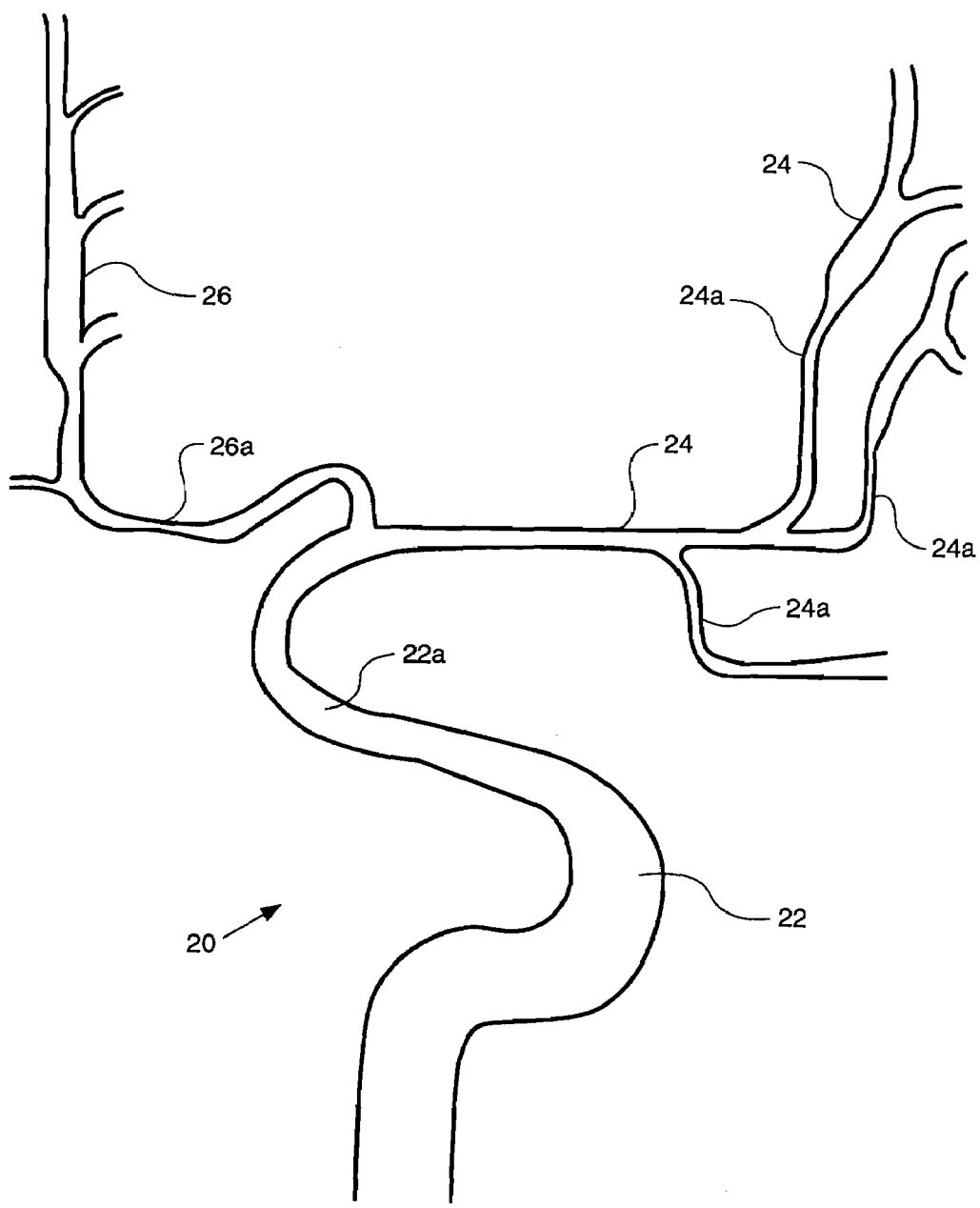
FIG. 3 is a schematic representation of the vascular anatomy of a brain with moderate vasospasm of the distal interior carotid artery, proximal anterior cerebral artery and proximal middle cerebral artery.

Referring now to FIG. 3, another schematic representation of the vascular anatomy of the brain 20 is shown. As illustrated the vessels are affected by moderate vasospasm. Vasospasm is represented by the narrowing of the vessels; specifically ICA 22 is narrowed at the distal segment 22a; MCA 24 is narrowed at the proximal segment 24a; and ACA 26 is narrowed at proximal segment 26a. This narrowing can be a byproduct of an event such as a ruptured brain aneurysm, known as subarachnoid hemorrhage (or SAH). Subsequent to the SAH a patient can develop intracranial vasospasm. As noted above, in vasospasm, the arteries supplying the brain are narrowed as a result of constriction and/or thickening of the blood vessel wall. Because the narrowed vessel lumen restricts blood flow, lack of blood supply to the brain distally can result in a stroke.

Figure 4A:
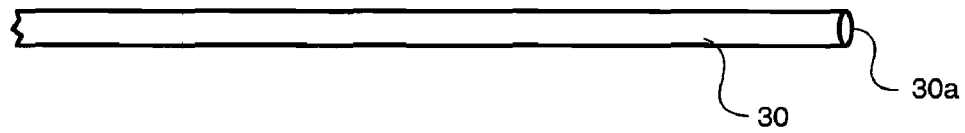
FIG. 4a is an elevational view of a known microcatheter used for dilatation when a balloon microcatheter cannot be advanced into a spastic vessel.

Referring to FIGS. 4a, 4b, 4c and 4d, the prior devices and methods used to treat vasospasm are shown so as to provide a departure for the discussion of the device and method of the present invention. As shown in FIG. 4a, a microcatheter 30 is shown of a type well known in the art, that while designed as a delivery system for coils or liquid agents, has in rare reports also been used to perform mechanical dilatation of smaller diameter branches in vasospasm. The diameter of the microcatheter 30 however would be too small to accomplish angioplasty in larger vessels in vasospasm (see, e.g., FIG. 6). Catheter 30 can be advanced in a vessel to point of narrowing of the vessel and, by virtue of its size, dilate the vessel. Further, catheter 30 may also be utilized as a delivery device for pharmacological agents that can dilate the vessel. However, in order to be effective, catheter 30 must be of a configuration, size and flexibility to reach to the point of constriction without damaging vessel walls.

Figure 4B:
FIG. 4b is an elevational view of an uninflated balloon microcatheter.
Figure 4C:
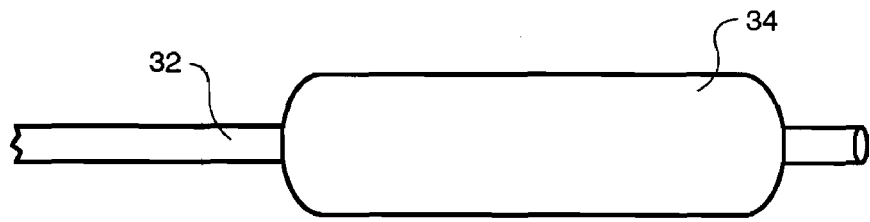
FIG. 4c is an elevational view of an inflated balloon microcatheter.

FIGS. 4b and 4c are, respectively, depictions of a balloon microcatheter 32, in a first uninflated state and a second inflated state. In the use of microcatheter 32, the catheter 32 is advanced into the vessel to the narrowed point and the balloon 34 is then inflated to dilate the narrowed vessel. The balloon 34 can be coated with pharmacological agents that, in cooperation with the inflation effect of the balloon, deliver dilating agents to the vessel's interior walls when inflated.

Figure 4D:
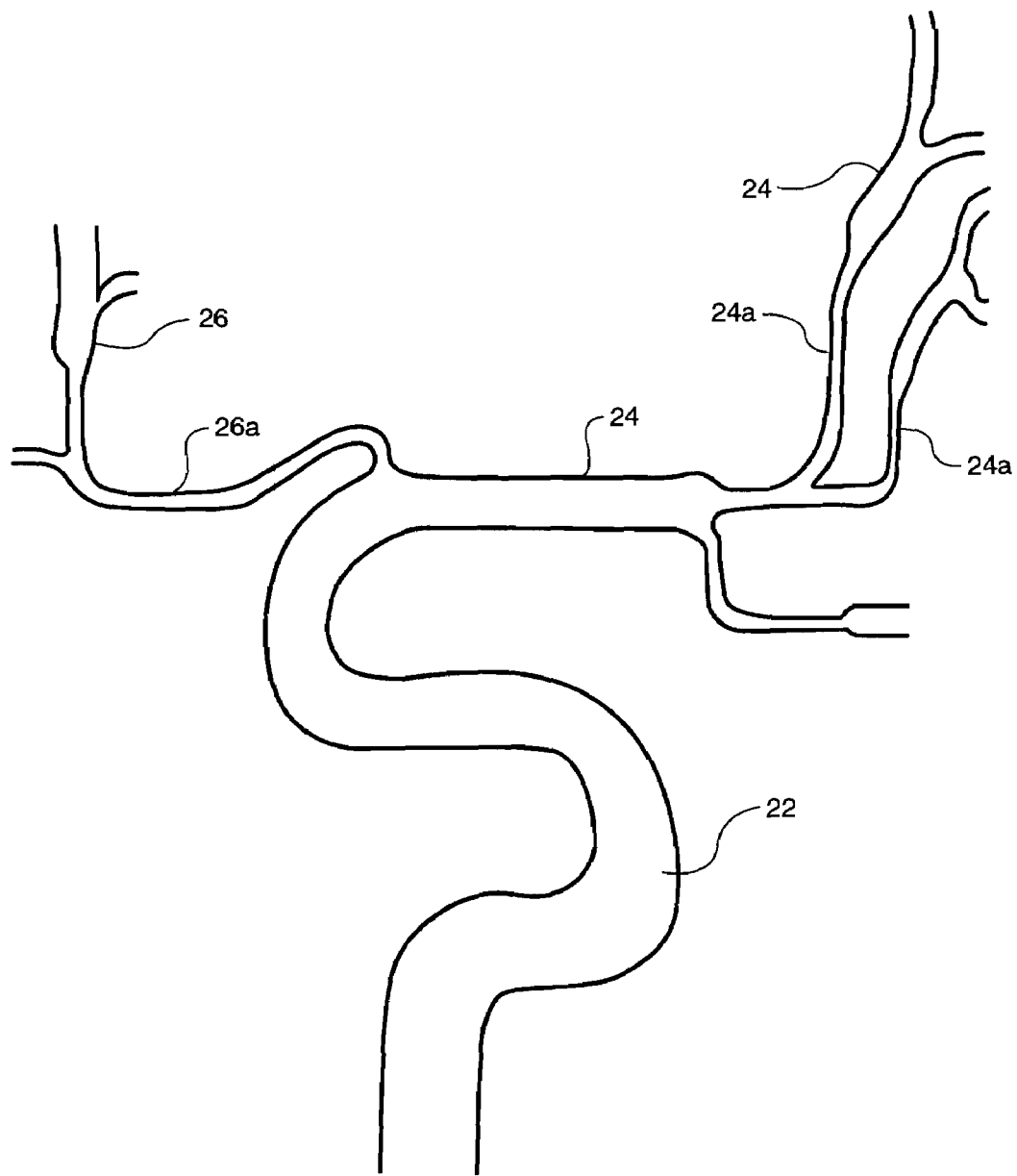
FIG. 4d is a schematic representation of the vascular anatomy of the brain of FIG. 3 after treatment by angioplasty with a typical balloon catheter showing improved diameter of the interior cerebral artery and a segment (M1), but in which areas (A1, A2 and M2) were unable to be treated, that is, illustrating that caliber is improved proximally but not distally.

However, as set forth above, such balloon catheters suffer from limited (large) diameters and stiffnesses that prevent use in small or more tortuous arterial networks. FIG. 4d illustrates the schematic arterial representation post angioplasty using the devices of FIG. 4b/4c. It will be seen in FIG. 4d that the use of the balloon catheter 32 provides adequate treatment of the ICA 22 and MCA segment M1 24a, but does not allow treatment of narrowed smaller diameter segments of the ACA 26 (segments 26a) and the MCA 24 (segments 24a).

Figure 5:
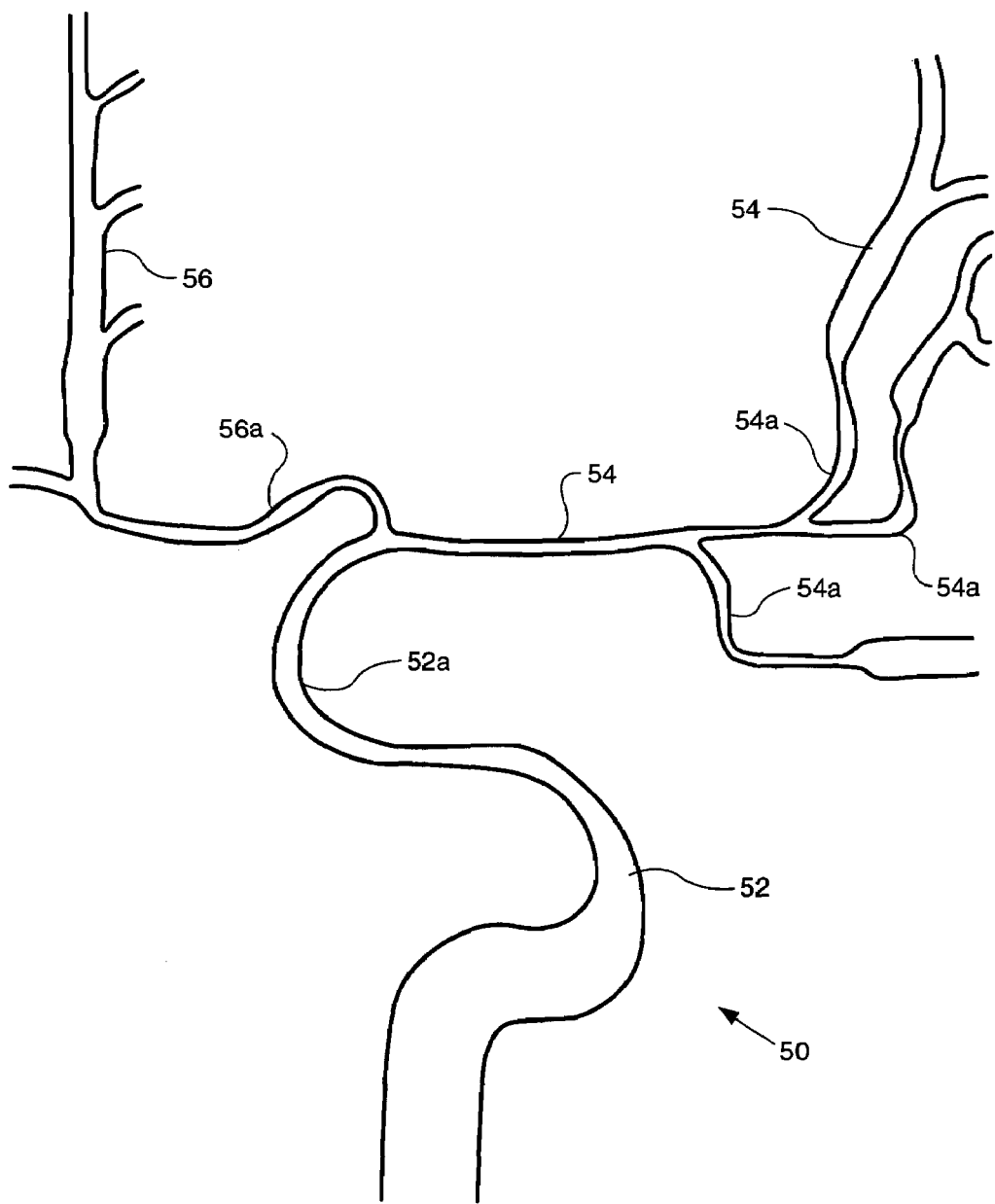
FIG. 5 is a schematic representation of the vascular anatomy of a brain with severe vasospasm of the distal interior carotid artery, proximal anterior cerebral artery and proximal middle cerebral artery.
Figure 6:
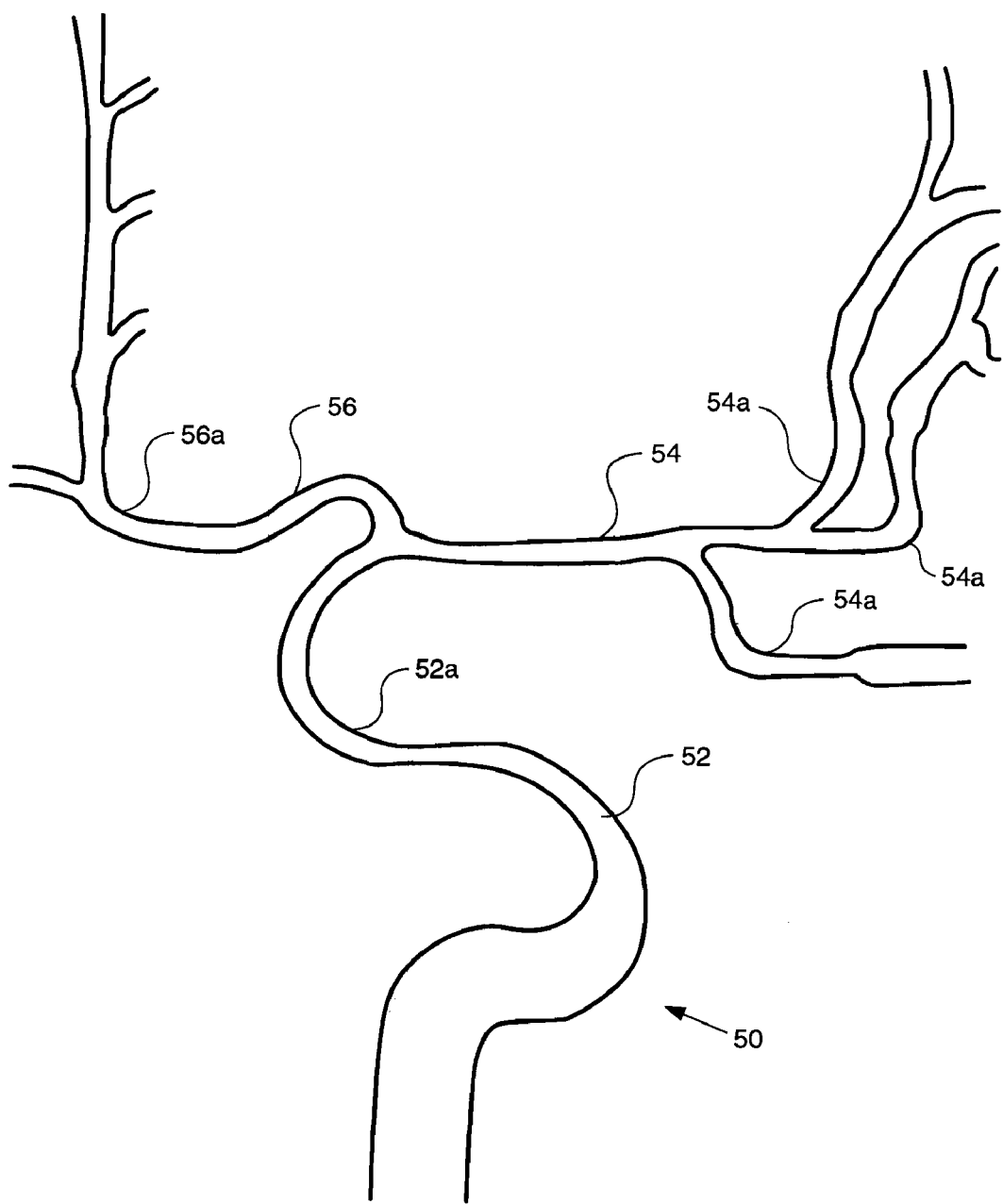
FIG. 6 is a schematic representation of the vascular anatomy of the brain of FIG. 5 following angioplasty with a typical microcatheter (illustrating that caliber is improved distally by not proximally).

Referring to FIG. 5, another schematic representation of the vascular anatomy of the brain 50 is shown. In this instance the vessels are suffering from severe vasospasm. Vasospasm is represented by the narrowing of the vessels; specifically ICA 52 is narrowed at the distal segment 52a; MCA 54 is narrowed at the proximal segment 54a; and ACA 56 is narrowed at proximal segment 56a. FIG. 6 shows a best-case scenario of the treatment, using the microcatheter 30 of FIG. 4a. A comparison of the vascular anatomy of FIGS. 1, 5, and 6 shows that the treatment used, that is the use of catheter 30 (FIG. 4a) resulted in improved diameters in ACA segments A1 (56) and A2 (56a) and MCA segment M2 (54a), as well as minimal or mild improvements in M1 segment (54) of MCA, but no significant improvement in ICA (52). The limited benefit in M1 segment (54) of MCA and the lack of improvement in ICA (52) is due to the catheter 30 having, initially, a smaller diameter than the narrowed segment 52a and therefore offering no dilation therein.

Figure 7:
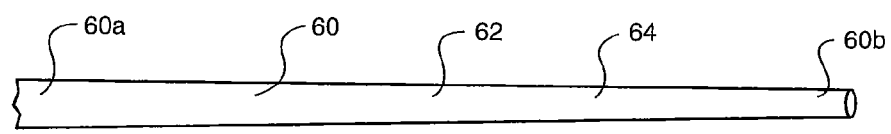
FIG. 7 is an elevational view of the device of the present invention.

Referring now to FIG. 7, the improved catheter 60 of the present invention is shown. It will be seen that catheter 60 tapers, more steeply than prior art catheters, from its proximal end 60a to its distal end 60b. Further, catheter 60 has a larger shaft than prior art catheters, a smaller tip, a steeper or more severe taper and thicker walls. The catheter can be braided to permit the catheter to be pushed further without kinking.

As seen in FIG. 7, the inner lumen 66 diameter $D_{66}$ of catheter 60 can be reduced to achieve thicker walls. Catheter 60, in a preferred embodiment, can be coated with performance enhancing lubricants 62, such as hydrophilic coating and with pharmacological agents 64 such as heparin, antiplatelet drugs, vasoactive drugs and the like. It will be understood that catheter 60 can be coated with other lubricating agents and other drugs and pharmacological agents, as well as other agents that can produce desirable effects (whether understood at present or not) without departing from the novel scope of the present invention.

In the use of the device of the present invention, catheter 60 is advanced into the vascular system shown in any of the previous figures. Because of the taper and the narrow, non-blunt tip, the catheter can be used to physically dilate smaller, more tortuous vessels while the larger proximal segment simultaneously dilates the larger M1 segment of MCA and the ICA. The advancement of catheter 60, thereby, dilates a significantly larger amount of the vascular system shown, while not causing damage that prior art catheters may be prone to cause. Additionally, catheter 60 can be used to deliver pharmacological agents further into the vascular system, as well, either through delivery as an injection through the end-hole or through imbedding the drug coating the catheter into the vessel wall inner lining in the process of angioplasty.

Figure 8:
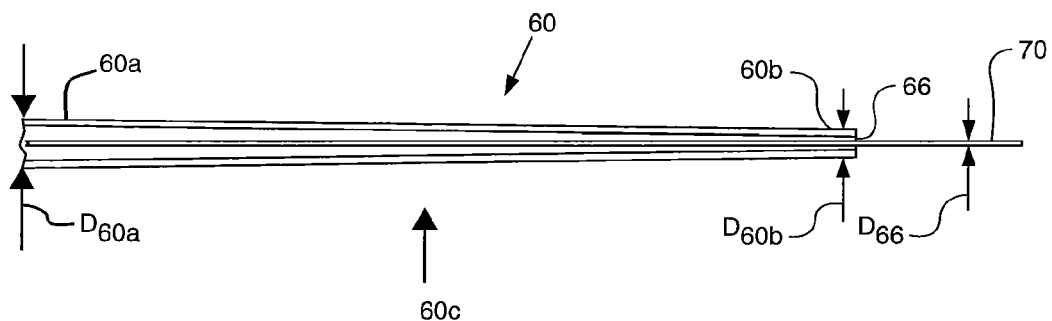
FIG. 8 is another elevational view of the device of the present invention.

As seen in FIG. 8, a presently contemplated catheter 60 has a length $L_{60}$ of about 120 cm to 150 cm, preferably about 130 cm. The diameter of the catheter is about 3 mm at the base or proximal end 60a $D_{60a}$ and tapers to a diameter $D_{60b}$ from about 0.67 mm to about 1 mm at the distal end 60b. The tapering of the catheter 60 occurs at about the distal most 20 cm to 30 cm (indicated at 60c), likely at about the distal most 20 cm. As discussed above, the diameter of the lumen $D_{66}$ is less than known catheters. The lumen 66 of the presently contemplated catheter has a diameter of about 14 thousandths of an inch (mils) to about 22 mils. It is anticipated that the catheter 60 is not necessarily used for the delivery of solid materials such as particulate agents or coils. Rather, the catheter may be used to deliver fluids such as drugs, and as such, the lumen diameter $D_{66}$ can remain relatively small. In such an arrangement, a lead wire 70 having a diameter of about 10 mils to 18 mils can be used.

It is anticipated that the thicker walls of the catheter 60 (in part permitted by the smaller lumen 66) will permit manipulating the catheter 60 into vessels that otherwise could not be reached by known catheters and dilating these vessels by movement of the catheter 60 therein. Advantageously, because the outside diameter of the proximal portion 60a of the present catheter 60 is larger and tip or distal portion 60b is smaller, the taper is steeper or more severe than known catheters. And, in that the taper occurs over the distal most 20 cm to 30 cm of the catheter, the present catheter 60 allows simultaneous dilatation of the various (caliber) cerebral arteries as the catheter is urged into the arterial system (e.g., toward and into the first, second and third order branches).

Those skilled in the art will recognize that the present device can be used in a like manner to effect improvement in vasospasm involving the vertebrobasilar system, and as such, the device and methods and use of the device and methods for such use are within the scope and spirit of the present invention.

In one embodiment of catheter 60, a catheter having no taper is provided with an expandable jacket 60 at its distal end. As the catheter is advanced into narrowed segments of vessels, the jacket can be expanded into the tapered shape desired to effect dilation. The catheter 60 may be comprised of a braided material, which in some circumstances may enhance pushability.

All patents referred to herein, are hereby incorporated herein by reference, whether or not specifically done so within the text of this disclosure.

Attributes of proposed angioplasty catheter include:
1) Steeper taper, much larger shaft.
   Alternative: Expandable jacket which achieves above configuration when jacket is expanded. Jacket is much longer than balloons currently available and expands to a tapered shape.
2) Catheter is thicker walled and braided to give more pushability (inner lumen diameter can be reduced to achieve thicker wall).
3) Catheter is coated with performance enhancing lubricant (hydrophilic coating).
4) Catheter is also coated with drugs and serves as a drug delivery device, drugs embedded into vessel intima (heparin, anti-platelet drugs, vasoactive drugs).

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover all such modifications as fall within the scope of the claims.

What is claimed is:

1. A microcatheter comprising:
   a single layer microcatheter having a proximal portion and a distal end portion;
   said proximal portion having an outside diameter of about 3 millimeters;
   said proximal portion extending to within a range of about 30 cm to about 20 cm from a distal end of said microcatheter;
   said distal end portion having an outside diameter between about 0.67 millimeters and about 1.0 millimeters;
   a taper from said outside diameter of said proximal portion to said outside diameter of said distal end portion;
   a lumen of substantially constant diameter, said lumen diameter being in a range between about 14 mils and about 22 mils; and
   whereby when said catheter is inserted into a human cranial arterial tree having narrowing in at least two of a first order branch, a second order branch and a third order branch, said catheter is positionable to therapeutically dilate said narrowing in at least one of said first, second or third order branches, and to simultaneously therapeutically dilate said narrowing in at least one other of the said first, second or third order branches, and said therapeutic dilation dilating the vessels to a healthier diameter.

2. The microcatheter in accordance with claim 1 wherein the microcatheter is formed as a braided element.

3. The microcatheter in accordance with claim 1 wherein the catheter has a coating thereon.

4. The micro catheter in accordance with claim 3 wherein the coating is a lubricant.

5. The microcatheter in accordance with claim 3 wherein the coating is a pharmacological agent.

6. The microcatheter in accordance with claim 5 wherein the pharmacological agent is an anticoagulant, an anti-platelet or a vasoactive agent.

7. The microcatheter in accordance with claim 1 wherein the length of the microcatheter is about 120 cm to about 150 cm.

8. The microcatheter in accordance with claim 1 including a lead wire and wherein the lead wire has a diameter of about 10 mils to about 18 mils.

9. The microcatheter of claim 1 wherein said tapered portion is less than about 30 centimeters long.

10. The microcatheter of claim 1 wherein said taper is continuous.

11. The microcatheter of claim 1 wherein said distal portion is continuously tapered to the distal end of the catheter.

12. The microcatheter of claim 1 wherein said first order vessel is a carotid artery, said second order vessel is selected from the group comprising an anterior cerebral artery, middle cerebral artery and posterior cerebral artery and said third order vessels are cerebral arteries distal to said second order arteries.

13. The microcatheter of claim 1 wherein the arteries are human intercranial artenes.

14. The micro catheter of claim 1 having a wall thickness between about 2.64 millimeters to about 0.11 millimeters.

* * * * *